(12) United States Patent
Gross et al.

(10) Patent No.: US 6,596,026 B1
(45) Date of Patent: Jul. 22, 2003

(54) TELESCOPIC INTRAOCULAR LENS

(75) Inventors: Yosef Gross, Moshav Mazor (IL); Gideon Dotan, Yehud (IL); Isaac Lipshitz, Herzelia Pituach (IL); Eli Aharoni, Kishon le Zion (IL)

(73) Assignee: Visioncare Ophthalmic Technologies, Inc., Saratoga, CA (US)

( * ) Notice: Subject to any disclaimer, the term of this patent is extended or adjusted under 35 U.S.C. 154(b) by 32 days.

(21) Appl. No.: 09/721,916

(22) Filed: Nov. 27, 2000

(51) Int. Cl.$^7$ .................................. A61F 2/16
(52) U.S. Cl. ............... 623/6.34; 623/6.25; 623/6.27
(58) Field of Search ............... 623/6.32, 6.33, 623/6.34, 6.38, 6.43, 6.17, 6.25, 6.28

(56) References Cited

U.S. PATENT DOCUMENTS

| | | | | |
|---|---|---|---|---|
| 4,074,368 A | * | 2/1978 | Levy, Jr. et al. ............ | 623/6.26 |
| 4,666,446 A | * | 5/1987 | Koziol et al. ............... | 623/6.62 |
| 4,892,543 A | * | 1/1990 | Turley ........................ | 623/6.62 |
| 5,133,745 A | * | 7/1992 | Falcetta et al. ............. | 623/6.26 |
| 5,201,762 A | * | 4/1993 | Hauber ....................... | 623/6.63 |
| 5,354,335 A | | 10/1994 | Lipshitz et al. | |
| 5,391,202 A | * | 2/1995 | Lipshitz et al. ............. | 623/6.62 |
| 5,476,515 A | * | 12/1995 | Kelman et al. ............. | 623/6.62 |
| 5,607,472 A | * | 3/1997 | Thompson .................. | 623/6.26 |
| 5,814,103 A | | 9/1998 | Lipshitz et al. | |
| 5,876,442 A | * | 3/1999 | Lipshitz et al. | |
| 5,928,283 A | | 7/1999 | Gross et al. | |
| 6,007,579 A | | 12/1999 | Lipshitz et al. | |
| 6,066,171 A | * | 5/2000 | Lipshitz et al. ............. | 623/6.18 |
| 6,187,042 B1 | * | 2/2001 | Sheets, Jr. et al. .......... | 623/6.62 |
| 6,357,875 B1 | * | 3/2002 | Herrick ...................... | 623/6.26 |
| 6,358,280 B1 | * | 3/2002 | Herrick ...................... | 623/6.26 |

* cited by examiner

Primary Examiner—David H. Willse
Assistant Examiner—Suzette J. Jackson
(74) Attorney, Agent, or Firm—Pillsbury Winthrop LLP

(57) ABSTRACT

An intraocular lens implant including a telescope body defining an optical path for light to pass therethrough, a positive lens and a negative lens attached to the telescope body, and mounting structure connected to the telescope body for mounting the implant in an eye, wherein the lenses abut against each other, and a distance between the positive lens and the negative lens is fixed and determined by the lenses abutting against each other.

9 Claims, 3 Drawing Sheets

TELESCOPIC INTRAOCULAR LENS

FIELD OF THE INVENTION

The present invention relates generally to intraocular lens (IOL) implants and particularly to a telescopic intraocular lens with novel, compact structure.

BACKGROUND OF THE INVENTION

Intraocular lens (IOL) inserts comprising telescopes are known. Representative examples of telescopic IOLs include applicant/assignee's U.S. Pat. Nos. 5,354,335; 5,391,202; 5,814,103; 5,876,442; 5,928,283; 6,007,579 and 6,066,171, the disclosures of which are incorporated herein by reference. Telescopic IOLs may be classified as Galilean, reverse Galilean, or telediopter. Galilean intraocular inserts have a positive (converging) lens at the anterior side of the eye and a negative (diverging) lens at the posterior side. Conversely, reverse Galilean intraocular inserts have a negative (diverging) lens at the anterior side of the eye and a positive (converging) lens at the posterior side.

Galilean telescopic IOLs are designed to correct problems stemming from central field defects, such as those caused by macular degeneration (e.g., atrophic or exudative), chorioretinitis of the macula, central serous chorioretinopathy, or ischemia, for example. Reverse Galilean telescopic IOLs are designed to correct problems stemming from peripheral field defects, such as those caused by retinitis pigmentosa, primary or metastatic central nervous system tumors or glaucoma, for example.

SUMMARY OF THE INVENTION

The present invention seeks to provide further improvements to telescopic IOLs. In one aspect of the present invention, the distance between the positive lens and negative lens is fixed and determined by the structure of the lenses abutting against each other. This novel structure saves on assembly and manufacturing costs.

In another aspect of the present invention, the lenses may be provided with different coatings for superior performance. For example, a yellow coating may be provided to improve night vision. A UV coating may be provided to protect against UV by day. A spectral coating may be provided to improve contrast. An anti-reflective coating may be provided to reduce reflections on the IOL.

In still another aspect of the present invention, the anterior and/or posterior faces of the IOL may be slanted with respect to a longitudinal axis (i.e., the anterior-posterior axis). This means that either the anterior or posterior faces (or both) are prismatic. Such a structure allows for "dialing" the IOL, i.e., rotating the IOL about the longitudinal axis in order to adjust the alignment of the IOL to suit the particular patient. Additionally or alternatively, the IOL is provided with a magnet, and a magnetic tool can be used to dial the IOL non-invasively by attracting the IOL magnet and appropriately turning the IOL.

In yet another aspect of the present invention, the IOL has a truncated cone shape, with one of the lenses being smaller in diameter than the other. Such a structure saves on material, volume and weight, and permits inserting the IOL with a smaller incision.

In another aspect of the present invention, the lenses of the IOL are packaged as separate "capsules" or housings which are aligned and joined, such as by bonding or snap-fitting together.

Different kinds of lenses may be used in the present invention, such as hologramic, graded index, diffractive, binary, multiorder diffractive, harmonic diffractive, Fresnel, spheric and aspheric.

There is thus provided in accordance with a preferred embodiment of the present invention an intraocular lens implant including a telescope body defining an optical path for light to pass therethrough, a positive lens and a negative lens attached to the telescope body, and mounting structure connected to the telescope body for mounting the implant in an eye, wherein the lenses abut against each other, and a distance between the positive lens and the negative lens is fixed and determined by the lenses abutting against each other.

In accordance with a preferred embodiment of the present invention at least one of the lenses is coated with at least one of a yellow coating, a UV coating, a spectral coating, and an anti-reflective coating.

Further in accordance with a preferred embodiment of the present invention the telescope body has an anterior face, a posterior face and a longitudinal axis, and at least one of the anterior and posterior faces are slanted with respect to the longitudinal axis of the telescope body.

Still further in accordance with a preferred embodiment of the present invention a magnet is mounted on a portion of the implant. Preferably a magnetic tool is provided to attract the magnet from outside an eye in which the implant is installable.

In accordance with a preferred embodiment of the present invention the telescope body has a truncated cone shape with one end having a greater diameter than an opposite end thereof.

Further in accordance with a preferred embodiment of the present invention one of the lenses is smaller than the other, and the smaller of the lenses is positioned near the smaller diameter end of the truncated cone shaped telescope body.

Additionally in accordance with a preferred embodiment of the present invention at least one of the lenses includes at least one of a diffractive lens, a binary lens, a multiorder diffractive lens, a harmonic diffractive lens, a Fresnel lens, a spheric lens and an aspheric lens.

There is also provided in accordance with a preferred embodiment of the present invention an intraocular lens implant including a positive lens mounted in a first housing, a negative lens mounted in a second housing, the first and second housings being aligned and joined together to define an optical path for light to pass therethrough, and mounting structure connected to at least one of the first and second housings for mounting the implant in an eye.

In accordance with a preferred embodiment of the present invention the first and second housings are bonded together. Alternatively, the first and second housings are snap-fit together.

There is also provided in accordance with a preferred embodiment of the present invention an intraocular lens implant including a telescope body defining an optical path for light to pass therethrough, the telescope body having end caps which substantially seal the telescope body, at least one lens attached inside the telescope body, and an air bubble substantially sealed inside the telescope body between the at least one lens and one of the end caps.

In accordance with a preferred embodiment of the present invention a plurality of the lenses are attached inside the telescope body, and at least one other air bubble is substantially sealed inside the telescope body between the lenses. Preferably the telescope body is made of glass.

BRIEF DESCRIPTION OF THE DRAWINGS

The present invention will be understood and appreciated more fully from the following detailed description, taken in conjunction with the drawings in which.

DETAILED DESCRIPTION OF A PREFERRED EMBODIMENT

Figure 1A:
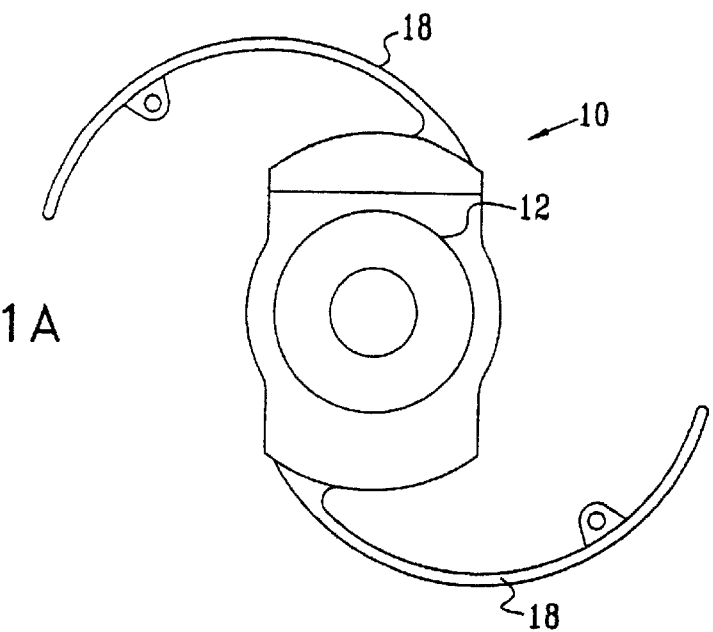
FIGS. 1A and 1B are simplified pictorial and partially sectional illustrations, respectively, of an intraocular lens implant constructed and operative in accordance with a preferred embodiment of the present invention, wherein a distance between a positive lens and a negative lens is fixed and determined by the structure of the lenses abutting against each other.
Figure 1B:
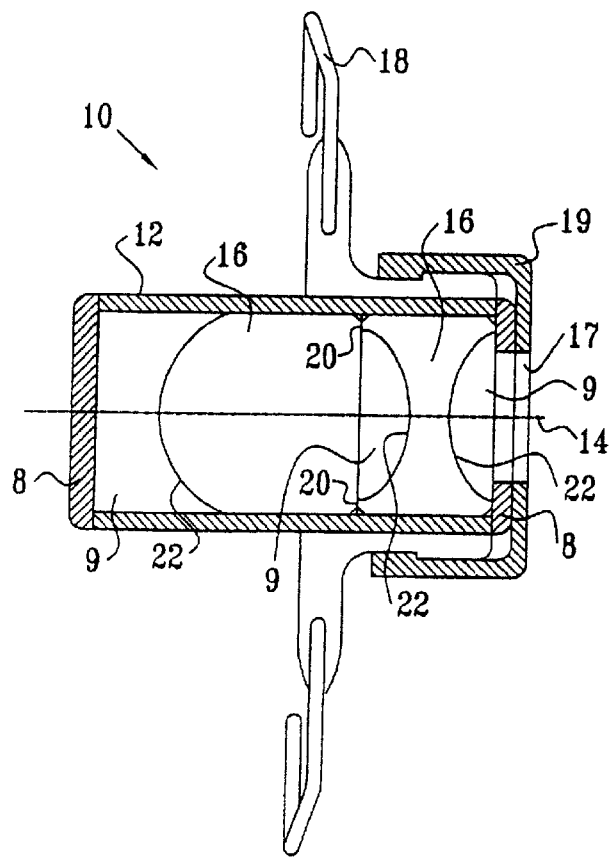

Reference is now made to FIGS. 1A and 1B which illustrate an intraocular lens (IOL) implant 10 constructed and operative in accordance with a preferred embodiment of the present invention. IOL implant 10 preferably includes a telescope body 12 defining an optical path 14 for light to pass therethrough. Telescope body 12 is preferably generally cylindrical and includes one or more lenses 16, preferably at least two, attached thereto. Most preferably, one of lenses 16 is positive and the other negative. In the illustrated embodiment, the positive lens is anteriorly positioned and the negative lens is posteriorly positioned, thereby forming a Gaussian telescopic system. It is appreciated that the lenses can be alternatively arranged to form a reverse Galilean telescopic system (having an anteriorly positioned negative lens and a posteriorly positioned positive lens).

Mounting structure 18 is provided for mounting IOL implant 10 in an eye (not shown). Mounting structure 18 may include, for example, one or more haptics extending from telescope body 12. A suitable material for constructing all parts of IOL implant 10, as is well known in the art, is polymethylmethacrylate (PMMA), for example.

In accordance with a preferred embodiment of the present invention, lenses 16 abut against each other. The distance between the two lenses 16 is fixed and determined by the lenses abutting against each other. Lenses 16 are preferably formed with chamfered and flattened surfaces 20 to facilitate lenses 16 abutting against each other. The lenses 16 may be joined to the inside of telescope body 12 by any suitable means, such as by bonding or welding, for example. An optical blocker 19 may be snapped onto the posterior end of telescope body 12. Optical blocker 19 preferably includes a translucent or opaque, generally cup-like cap with a generally centrally-located aperture 17 formed therein for passing light therethrough.

In accordance with a preferred embodiment of the present invention, telescope body 12 is made of glass with sealed end caps 8, preferably welded thereto. (The anterior end cap 8 is preferably formed with a generally centrally-located aperture for passing light therethrough.) In such a structure, there is an air bubble 9 between lenses 16 and between each of lenses 16 and each end cap 8. The light is refracted by air bubbles 9 as it passes through telescope body 12. Glass is the preferred material, because it makes a substantially hermetic seal, thereby ensuring the long-term presence and integrity of air bubbles 9.

In accordance with a preferred embodiment of the present invention, one or both of lenses 16 is provided with a coating 22 for superior performance. For example, coating 22 may be yellow to improve night vision. Alternatively, coating 22 may be a UV coating to protect against UV by day. As another alternative, coating 22 may be a spectral coating to improve contrast. Alternatively, coating 22 may be anti-reflective to reduce reflections on IOL implant 10.

Figure 2:
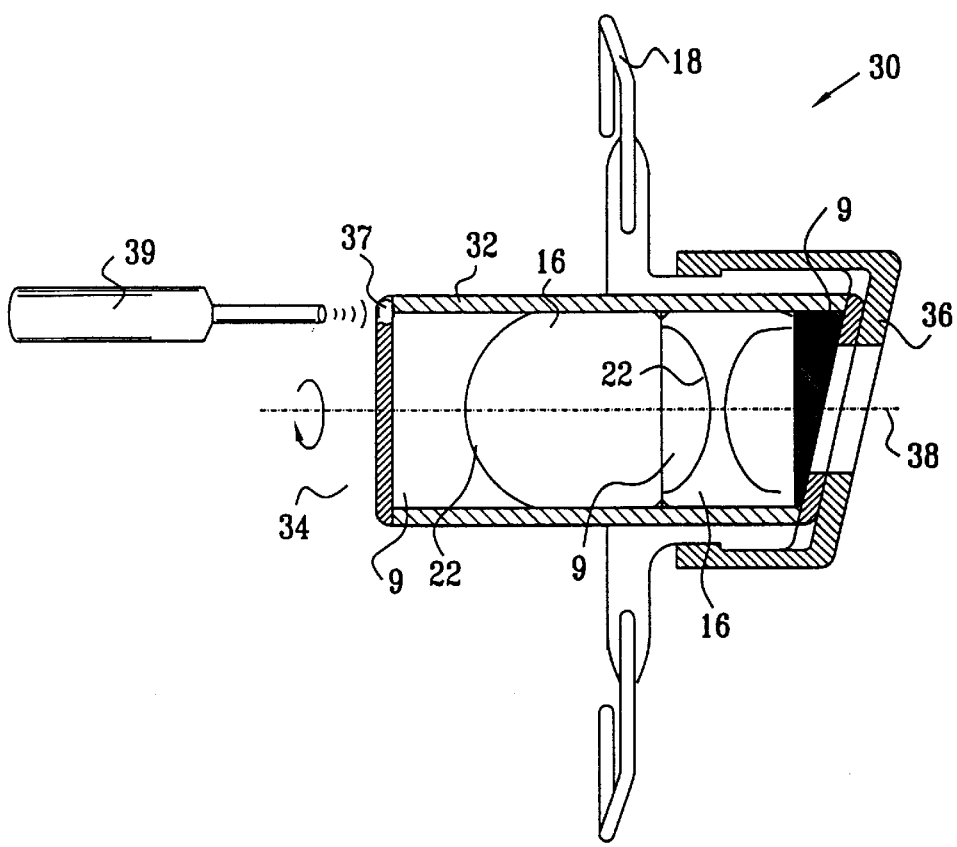
FIG. 2 is a simplified partially sectional illustration of an intraocular lens implant constructed and operative in accordance with another preferred embodiment of the present invention, wherein the posterior face of the IOL is slanted with respect to a longitudinal axis.

Reference is now made to FIG. 2 which illustrates an intraocular lens implant 30 constructed and operative in accordance with another preferred embodiment of the present invention. Implant 30 is preferably constructed similarly to implant 10, with like elements being designated by like numerals. Implant 30 includes a telescope body 32 that has an anterior face 34, a posterior face 36 and a longitudinal axis 38 (i.e., anterior-posterior axis). Implant 30 differs from implant 10, in that in implant 30, either or both of anterior and posterior faces 34 and 36 are slanted with respect to axis 38. This means that either anterior or posterior faces 34 or 36 (or both) are prismatic. Such a structure allows for "dialing" IOL implant 30, i.e., rotating the IOL about axis 38 in order to adjust the alignment of IOL implant 30 to suit the particular patient. Additionally or alternatively, implant 30 may be provided with a magnet 37 mounted on any part of the structure of implant 30, such as telescope body 32, mounting structure 18 (e.g., the haptics), or even a portion of lenses 16. A magnetic tool 39 can be used to dial implant 30 non-invasively by attracting magnet 37 and appropriately turning implant 30 about axis 38.

Figure 3:
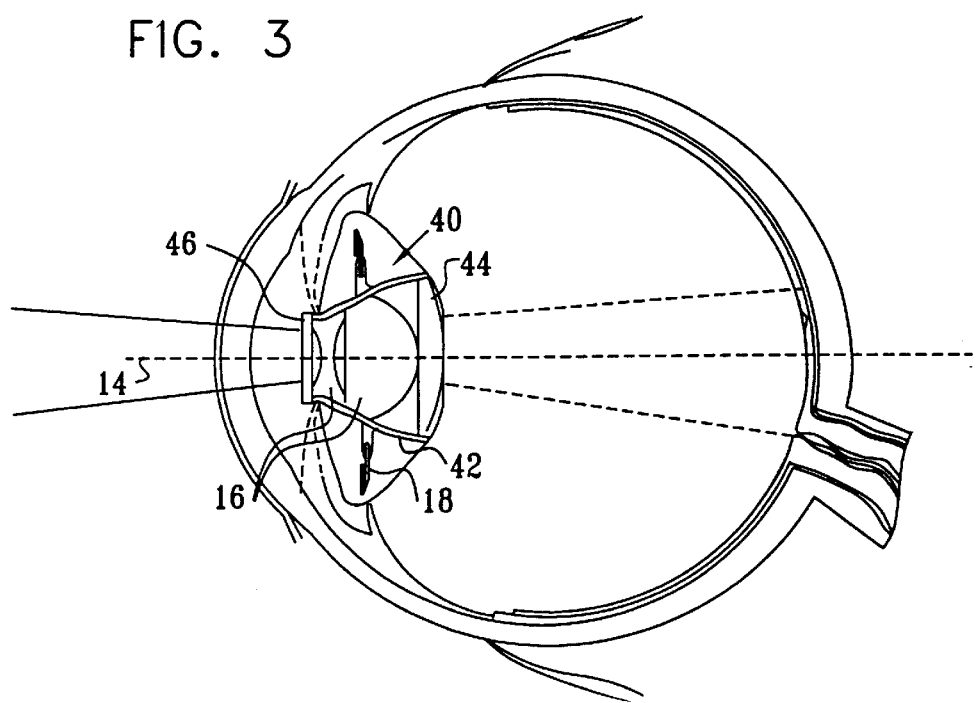
FIG. 3 is a simplified partially sectional illustration of an intraocular lens implant constructed and operative in accordance with yet another preferred embodiment of the present invention, wherein the IOL has a truncated cone shape.

Reference is now made to FIG. 3 which illustrates an intraocular lens implant 40 constructed and operative in accordance with yet another preferred embodiment of the present invention. Implant 40 is preferably constructed similarly to implant 10 or implant 30, with like elements being designated by like numerals. Implant 40 includes a telescope body 42 that has a truncated cone shape with one end 44 (in the illustration, the posterior end) having a greater diameter than an opposite end 46 thereof (in the illustration, the anterior end). In this embodiment, one of the lenses 16 (in the illustration, the anterior, negative lens) is preferably smaller than the other (in the illustration, the posterior, positive lens), and the smaller of the lenses is positioned near the smaller diameter end of the truncated cone shaped telescope body 42. Such a structure saves on material, volume and weight, and permits inserting implant 40 with a smaller incision.

Figure 4:
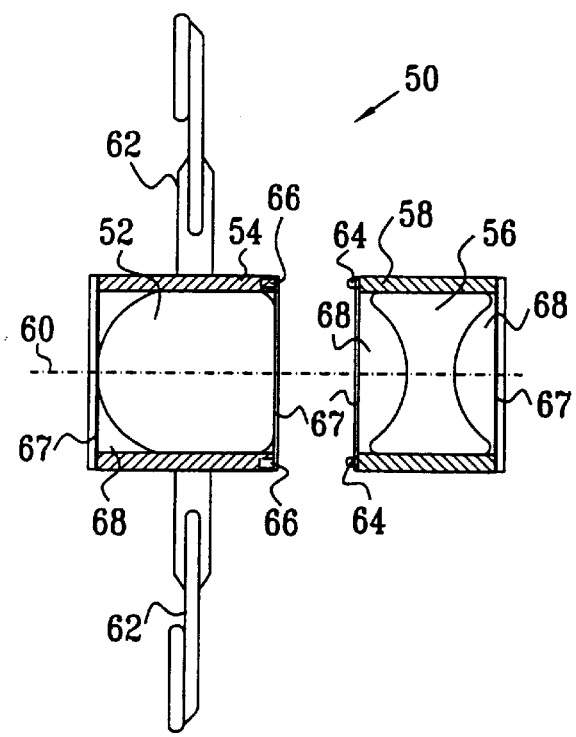
FIG. 4 is a simplified partially sectional illustration of an intraocular lens implant constructed and operative in accordance with another preferred embodiment of the present invention, wherein lenses of the IOL are packaged as separate "capsules" which are aligned and joined together.

Reference is now made to FIG. 4 which illustrates an intraocular lens implant 50 constructed and operative in accordance with another preferred embodiment of the present invention. IOL implant 50 preferably includes a positive lens 52 mounted in a first housing 54, and a negative lens 56 mounted in a second housing 58. First and second housings 54 and 58 (or "capsules") are aligned and joined together to define an optical path 60 for light to pass therethrough. Mounting structure 62 is preferably connected to first 54 and/or second housing 58 for mounting implant 50 in an eye. First and second housings 54 and 58 may be bonded together. Alternatively, first and second housings 54 and 58 may be snap-fit together, such as by means of male and female snap connectors 64 and 66, respectively, attached to or integrally formed with housings 54 and 58. First and second housings 54 and 58 together comprise a telescope body.

First and second housings 54 and 58 are preferably made of glass with sealed end caps 67 and air bubbles 68 between the end caps and the lenses, as similarly described hereinabove with reference to FIG. 1B.

It is noted that an IOL implant may be constructed in accordance with the present invention, including any combination of the embodiments shown and described above with reference to FIGS. 1–4.

In addition, any of the embodiments of the present invention may be made with different kinds of lenses 16, such as holographic, graded index, diffractive, binary, multiorder diffractive, harmonic diffractive, Fresnel, spheric and aspheric. Multiorder lenses are discussed in various optical texts and articles, such as Dean Faklis and G. Michael Morris, "Spectral Properties of Multiorder Diffractive Lenses", Applied Optics, Vol. 34, No. 14, May 10, 1995, particularly pages 2462–2474.

Figure 5A:
FIGS. 5A and 5B are simplified sectional illustrations of two different kinds of diffractive lenses useful in the intraocular lens implants of FIGS. 1–4, constructed and operative in accordance with two preferred embodiments of the present invention.
Figure 5B:
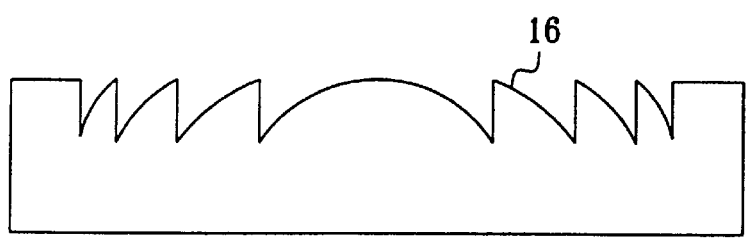

Two examples of diffractive lenses are shown in FIGS. 5A and 5B. FIG. 5A illustrates a binary, 4 level lens with a step phase shift of $2\pi/4$, $\eta=80\%$ and power$\approx\lambda$. FIG. 5B illustrates a harmonic Fresnel lens with a phase shift of $m2\pi$, $\eta=100\%$ and power$\approx\lambda$. Of course, these are just two examples of the many kinds of diffractive lenses possible within the scope of the invention.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. An intraocular lens implant comprising:
    a telescope body defining an optical path for light to pass therethrough;
    a positive lens and a negative lens attached to said telescope body; and
    mounting structure connected to said telescope body for mounting said implant in an eye, wherein said lens abut against each other, and a space or distance between said positive lens and said negative lens is fixed and determined by said lenses abutting against each other.

2. The intraocular lens implant according to claim 1, wherein at least one of said lenses is coated with at least one of a yellow coating, a UV coating, a spectral coating, and an anti-reflective coating.

3. The intraocular lens implant according to claim 1, wherein said telescope body has an anterior face, a posterior face and a longitudinal axis, and at least one of said anterior and posterior faces are slanted with respect to said longitudinal axis of said telescope body.

4. An intraocular lens implant comprising:
    a telescope body defining an optical path for light to pass therethrough;
    at least one lens attached to said telescope body;
    mounting structure connected to said telescope body for mounting said implant in an eye, wherein said at least one lens comprises a multiorder diffractive lens.

5. The intraocular lens implant according to claim 4, wherein said at least one lens comprises a positive lens and a negative lens, said lenses abutting against each other, and wherein a distance between said positive lens and said negative lens is fixed and determined by said lenses abutting against each other.

6. The intraocular lens implant according to claim 4, wherein said at least one lens is coated with at least one of a yellow coating, a UV coating, a spectral coating, and an anti-reflective coating.

7. An intraocular lens implant comprising:
    a telescope body defining an optical path for light to pass therethrough, said telescope body having end caps which substantially seal said telescope body;
    at least one lens attached inside said telescope body; and
    an air bubble substantially sealed inside said telescope body between said at least one lens and one of said end caps.

8. The intraocular lens implant according to claim 7 and further comprising a plurality of said lenses attached inside said telescope body, and at least one other air bubble substantially sealed inside said telescope body between said lenses.

9. The intraocular lens implant according to claim 7 wherein said telescope body is made of glass.

* * * * *